US012799063B2

(12) United States Patent
Tose et al.

(10) Patent No.: US 12,799,063 B2
(45) Date of Patent: Nov. 17, 2026

(54) METHOD FOR PRODUCING GLYCOLIDE

(71) Applicant: Kureha Corporation, Tokyo (JP)

(72) Inventors: Takenori Tose, Tokyo (JP); Yoshinori Suzuki, Tokyo (JP); Toshihiko Ono, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 594 days.

(21) Appl. No.: 18/550,062

(22) PCT Filed: Feb. 7, 2022

(86) PCT No.: PCT/JP2022/004660

§ 371 (c)(1),
(2) Date: Sep. 11, 2023

(87) PCT Pub. No.: WO2022/196178

PCT Pub. Date: Sep. 22, 2022

(65) Prior Publication Data

US 2024/0182397 A1 Jun. 6, 2024

(30) Foreign Application Priority Data

Mar. 16, 2021 (JP) ................................. 2021-042775

(51) Int. Cl.
*C07C 51/09* (2006.01)
*C07D 319/12* (2006.01)

(52) U.S. Cl.
CPC ............ *C07C 51/09* (2013.01); *C07D 319/12* (2013.01)

(58) Field of Classification Search
None
See application file for complete search history.

(56) References Cited

U.S. PATENT DOCUMENTS

| | | | |
|---|---|---|---|
| 5,871,919 | A | 2/1999 | Brant et al. |
| 6,916,939 | B2 | 7/2005 | Yamane et al. |
| 8,981,124 | B2 | 3/2015 | Wautier |
| 2003/0191326 | A1 | 10/2003 | Yamane et al. |
| 2010/0298578 | A1 | 11/2010 | Chang et al. |
| 2013/0116448 | A1 | 5/2013 | Wautier |
| 2021/0087162 | A1 | 3/2021 | Yamaji et al. |

FOREIGN PATENT DOCUMENTS

| | | | |
|---|---|---|---|
| CN | 103003261 | A | 3/2013 |
| EP | 588222 | A2 | 3/1994 |
| JP | 6-172341 | A | 6/1994 |
| JP | 2013-535433 | T | 9/2013 |
| JP | 2014-185116 | A | 10/2014 |
| JP | 2019-99540 | A | 6/2019 |
| KR | 10-2012-0009879 | A | 2/2012 |
| WO | 02/14303 | A1 | 2/2002 |
| WO | 2019/181516 | A1 | 9/2019 |

OTHER PUBLICATIONS

Translation of Yamadoi (JP2019099540A, published on Jun. 24, 2019), obtained Apr. 8, 2026 (Year: 2026).*
112-98-1 (SciFinder entry of tetraethylene glycol dibutyl ether, obtained on Apr. 9, 2026) (Year: 2026).*
19327-38-9 (SciFinder entry of octyl triethylene glycol, obtained on Apr. 9, 2026) (Year: 2026).*
26009-03-0 (SciFinder entry of polyglycolic acid, obtained on Apr. 9, 2026) (Year: 2026).*
Extended European Search Report for European Application No. 22770937.5, dated Jul. 31, 2024.
English translation of International Preliminary Report on Patentability and Written Opinion of the International Searching Authority for International Application No. PCT/JP2022/004660, dated Sep. 28, 2023.
Chinese Office Action and Search Report for Chinese Application No. 202280015824.9, dated May 9, 2025, with English translation.
Chinese Office Action for Chinese Application No. 202280015824.9, dated Sep. 6, 2025, with English translation.
European Communication pursuant to Article 94(3) EPC for European Application No. 22 770 937.5, dated Jul. 30, 2026.

* cited by examiner

*Primary Examiner* — Amy C Bonaparte
(74) *Attorney, Agent, or Firm* — Birch, Stewart, Kolasch & Birch, LLP

(57) ABSTRACT

To realize a method for producing glycolide that suppresses generation of by-products while productivity of glycolide is improved. A method for producing glycolide, the method including: a first step of preparing a depolymerization reaction solution containing a glycolic acid oligomer and a titanium catalyst selected from the group consisting of organic titanium catalysts and inorganic titanium catalysts, and a second step of producing glycolide by depolymerization of the glycolic acid oligomer, a content of titanium element derived from the titanium catalyst in the depolymerization reaction solution being 1.2 mmol/L or less.

6 Claims, No Drawings

METHOD FOR PRODUCING GLYCOLIDE

TECHNICAL FIELD

The present invention relates to a method for producing glycolide.

BACKGROUND ART

Glycolide has been used as a starting raw material of polyglycolic acid that is useful for production of biodegradable polymers, medical polymers, and the like. In such a circumstance, an efficient method for producing glycolide has been demanded.

Patent Document 1 describes improvement in productivity of glycolide caused by adding titanium alkoxide during heating of α-hydroxy acid. Furthermore, Patent Document 2 describes improvement in production speed of glycolide by adding a metallic titanium in a glycolic acid aqueous solution and supplying it to a glycolic acid oligomer.

CITATION LIST

Patent Literature

Patent Document 1: JP 2013-535433 T
Patent Document 2: WO 2019/181516

SUMMARY OF INVENTION

Technical Problem

However, known techniques like those describe above improve productivity of glycolide but generate a large amount of by-products. Due to the generation of by-products, the purity of produced glycolide decreases. Furthermore, when production of glycolide continues for a long period of time, by-products may be accumulated in a reaction solution, and stable production of glycolide may become difficult. Therefore, development of a production method that suppresses generation of by-products while high productivity of glycolide is maintained has been an issue.

Solution to Problem

To solve the problems described above, the present invention is a method for producing glycolide. The method for producing glycolide includes a first step of preparing a depolymerization reaction solution containing a glycolic acid oligomer and a titanium catalyst selected from the group consisting of organic titanium catalysts and inorganic titanium catalysts; and a second step of producing glycolide by depolymerization of the glycolic acid oligomer, and a content of titanium element derived from the titanium catalyst in the depolymerization reaction solution is 1.2 mmol/L or less.

Advantageous Effects of Invention

The method for producing glycolide according to an embodiment of the present invention has effects of maintaining production speed of glycolide and suppressing generation of by-products.

DESCRIPTION OF EMBODIMENTS

A preferred embodiment for carrying out the present invention will now be explained. Note that the embodiment explained below illustrates a representative embodiment of the present invention, and it should not be interpreted that the scope of the present invention is narrowed by this embodiment.

Method for Producing Glycolide

Next, the method for producing glycolide of the present embodiment will be described. The method for producing glycolide according to the present embodiment includes: a first step of preparing a depolymerization reaction solution containing a glycolic acid oligomer and a titanium catalyst selected from the group consisting of organic titanium catalysts and inorganic titanium catalysts, and a second step of producing glycolide by depolymerization of the glycolic acid oligomer, a content of titanium element derived from the titanium catalyst in the depolymerization reaction solution being 1.2 mmol/L or less. By this configuration, generation of by-products can be suppressed while productivity of glycolide is improved.

In the present embodiment, "improvement of productivity of glycolide" refers to improvement of production speed of glycolide by a catalyst. The improvement of production speed of glycolide can be evaluated based on the change in the production speeds (g/h) of crude glycolide before and after catalyst addition in the depolymerization reaction in the second step. The production speed of the crude glycolide is evaluated using a production speed ratio calculated by dividing a production speed of crude glycolide after catalyst addition by a production speed of crude glycolide before the catalyst addition. The production speed ratio of the crude glycolide of 1.1 or greater can be evaluated as the productivity of glycolide being improved.

In the present embodiment, "suppression of generation of by-products" indicates that production speed of by-products is not increased by a catalyst. The suppression of generation of by-products can be evaluated by change in contents (wt. %/h) of by-products in the crude glycolide before and after the catalyst addition. The production speed of by-products is evaluated using a production speed ratio calculated by dividing a production speed of by-products after catalyst addition by a production speed of by-products before the catalyst addition. The production speed ratio of by-products of 1.4 or less can be evaluated as generation of by-products being suppressed. The production speed ratio of by-products is preferably 1.10 or less, more preferably 1.05 or less, and particularly preferably 1.0 or less.

Note that the content (wt. %/h) of by-products in the crude glycolide may be 0.85 or less or is preferably 0.65 or less from the perspective of producing glycolide having a high purity.

In the second step of the present embodiment, the glycolide is obtained as crude glycolide containing glycolide and by-products. Hereinafter, in a case where consideration of by-products contained in the crude glycolide is not necessary, the crude glycolide may be simply referred to as glycolide.

In the present embodiment, typical examples of by-products include methyl glycolide and acetoxyacetic acid.

First Step

The first step prepares a depolymerization reaction solution containing, as components, a glycolic acid oligomer and a titanium catalyst selected from the group consisting of organic titanium catalysts and inorganic titanium catalysts. In the present embodiment, the "depolymerization reaction solution" refers to a solution supplied to a depolymerization reaction in the second step. The first step is only required to prepare the depolymerization reaction solution containing the components, and the preparation method of each component, the preparation method of the depolymerization reaction solution, and other components contained in the depolymerization reaction solution are not particularly limited.

The weight average molecular weight (Mw) of the glycolic acid oligomer is preferably 1000 or greater and 100000 or less, and more preferably 10000 or greater and 100000 or less, from the perspective of the glycolide yield. The weight average molecular weight (Mw) can be measured by gel permeation chromatography.

From the perspective of the yield of glycolide for the depolymerization reaction, the melting point (Tm) of the glycolic acid oligomer is, for example, preferably 140° C. or higher, more preferably 160° C. or higher, and even more preferably 180° C. or higher. The upper limit of the melting point (Tm) of the glycolic acid oligomer is, for example, 220° C. The melting point (Tm) of the glycolic acid oligomer can be measured from the endothermic peak temperature when the glycolic acid oligomer is heated at a rate of 10° C./min in an inert gas atmosphere using a differential scanning calorimeter.

Titanium Catalyst

The titanium catalyst contained in the depolymerization reaction solution is an organic titanium catalyst or an inorganic titanium catalyst. The titanium catalyst is only required to be soluble in the depolymerization reaction solution.

The content of the titanium element derived from the titanium catalyst in the depolymerization reaction solution is 1.2 mmol/L or less, and more preferably 1.0 mmol/L or less. The content of the titanium element derived from the titanium catalyst in the depolymerization reaction solution in this range allows suppression of generation of by-products while productivity of the glycolide is improved.

In a preferred aspect, the content of the titanium element in the depolymerization reaction solution is 0.008 mmol/L or greater, and more preferably 0.01 mmol/L or greater. The content of the titanium element in the depolymerization reaction solution in this range allows suitable improvement in productivity of glycolide.

The organic titanium is not particularly limited. Examples of the ligand of the organic titanium include ionic ligands or neutral ligands, such as alkoxide, carboxide, benzoxide, an amine anion, a cyanide compound ion, a sulfur compound ion, a cyclopentadienyl anion, acetylacetone, pyridine, triphenylphosphine, ethylenediamine, bipyridine, phenanthroline, BINAP, catecholate, terpyridine, ethylenediaminetetraacetic acid, porphyrin, cyclam, and crown ether. One type or a plurality of types of these ligands may be coordinated to one titanium element.

The inorganic titanium is an inorganic titanium containing no metallic titanium and is not particularly limited. Examples of the ligand of the inorganic titanium include a hydride ion, a halide ion, a hydroxide ion, a cyanide ion, a nitrate ion, a nitrite ion, a hypochlorite ion, a chlorite ion, a chlorate ion, a perchlorate ion, a permanganate ion, a hydrogencarbonate ion, a dihydrogen phosphate ion, a hydrogen sulfate ion, a hydrogen sulfide ion, a superoxide ion, an oxide ion, a sulfide ion, a peroxide ion, a sulfate ion, a sulfite ion, a thiosulfate ion, a carbonate ion, a chromate ion, a dichromate ion, a monohydrogen phosphate ion, and a phosphate ion. One type or a plurality of types of these ligands may be coordinated to one titanium element.

The titanium catalyst is preferably an organic titanium catalyst. Since the organic titanium catalyst dissolves in the depolymerization reaction solution and also has high activity, the organic titanium catalyst is suitably used as a catalyst for depolymerization of glycolide.

The organic titanium catalyst preferably contains a titanium alkoxide. The titanium alkoxide is not particularly limited, and examples thereof include titanium tetramethoxide, titanium tetraethoxide, titanium tetra-n-propoxide, titanium tetraisopropoxide, titanium tetra-n-butoxide, titanium tetraisobutoxide, titanium tetra-n-pentoxide, titanium tetraisopentoxide, titanium tetra-n-hexoxide, titanium tetra-n-heptoxide, titanium tetra-n-octoxide, titanium tetra-2-ethylhexoxide, titanium tetracyclohexoxide, and titanium tetraphenoxide. The form of the titanium catalyst is only required to be a form that can be charged in a reactor and may be a liquid, powder, plate, wire, or block form. Among these, from the perspective of ease of uniform dispersion in the depolymerization reaction solution, the titanium catalyst is preferably a liquid.

Metallic titanium catalysts that are used in the related art require a process of heating for a long time period during catalyst dissolution. On the other hand, since the organic titanium or the inorganic titanium dissolves rapidly in a solvent, a heating process is not necessary during titanium catalyst dissolution. Thus, use of the organic titanium and the inorganic titanium in glycolide production is preferable from the perspective of shortening glycolide production cycle time.

The organic titanium catalyst is a highly active catalyst in production of glycolide. Thus, the organic titanium catalyst can be suitably used in glycolide production. Among these, since a titanium alkoxide is for a wide use at a low cost, the titanium alkoxide can be particularly preferably used.

Solvent

The depolymerization reaction solution of the present embodiment may contain an optional solvent. For example, in a case where a solvent is not contained, reaction of a liquid phase at a temperature not lower than the melting point of the glycolic acid oligomer is preferred. Consequently, the catalyst is uniformly dispersed in the glycolic acid oligomer, and thus depolymerization reaction of the glycolic acid oligomer can be suitably caused in the second step described below.

In a case where the depolymerization reaction solution contains a solvent, the solvent is not particularly limited as long as the solvent can depolymerize the glycolic acid, and the depolymerization reaction solution preferably contains an organic solvent. Use of the organic solvent enables prevention of attachment of glycolide and the like to an inner wall of a production line, in addition to action as a co-distilled component when formed glycolide is removed from the reaction system.

From the perspective of appropriately increasing the depolymerization reaction temperature in the second step and facilitating an increase in the production speed of glycolide, the organic solvent contained in the depolymerization reaction solution preferably includes a high boiling point organic solvent having a boiling point of 230° C. or higher and 450° C. or lower, preferably 235° C. or higher and 450° C. or lower, more preferably 255° C. or higher and 430° C. or lower, and even more preferably 280° C. or higher and 420° C. or lower.

Furthermore, the molecular weight of the organic solvent is preferably from 150 to 450, more preferably from 180 to 420, and particularly preferably from 200 to 400. The molecular weight of the organic solvent within the range described above facilitates occurrence of codistillation with glycolide.

Examples of such high boiling point organic solvents include aromatic dicarboxylic acid diesters, aromatic carboxylic acid esters, aliphatic dicarboxylic acid diesters, polyalkylene glycol diethers, aromatic dicarboxylic acid dialkoxyalkyl esters, aliphatic dicarboxylic acid dialkoxyalkyl esters, polyalkylene glycol diesters, and aromatic phosphoric acid esters. Among these, organic solvents including aromatic dicarboxylic acid diesters, aromatic carboxylic acid esters, aliphatic dicarboxylic acid diesters, and polyalkylene glycol diethers are preferable, and from the perspective of being less likely to cause thermal degradation, an organic solvent including a polyalkylene glycol diether represented by Formula (1) below is more preferable.

[Chemical Formula 1]

$$X—O—(—R—O—)p\text{-}Y \quad (1)$$

In Formula (1). R represents a methylene group or a linear or branched alkylene group having from 2 to 8 carbons, X and Y each independently represent an alkyl group having from 2 to 20 carbons or an aryl group, p represents an integer of 1 to 5, and when p is 2 or greater, a plurality of Rs may be the same or different.

X in Formula (1) is a hydrocarbon group, such as an alkyl group or an aryl group and, among these, is preferably a hydrocarbon group having from 1 to 20 carbons. Examples of the alkyl group include a methyl group, an ethyl group, a propyl group, a butyl group, a pentyl group, a hexyl group, a heptyl group, an octyl group, a nonyl group, a decyl group, and a lauryl group. These alkyl groups may be branched or linear. Examples of the aryl group include a phenyl group, a naphthyl group, a substituted phenyl group, and a substituted naphthyl group. The substituent of the substituted phenyl group or the substituted naphthyl group is preferably an alkyl group, an alkoxy group, or a halogen atom (e.g., Cl, Br, or I). The number of such substituents is, for example, from 1 to 5 and preferably from 1 to 3 in the case of a substituted phenyl group. In the case where a plurality of substituents are present, the substituents may be the same or different. Note that such a substituent serves to adjust the boiling point and the polarity of the polyalkylene glycol diether.

The molecular weight of the polyalkylene glycol diether is preferably from 150 to 450, more preferably from 180 to 420, and even more preferably from 200 to 400.

Examples of the polyalkylene glycol diether include a polyalkylene glycol dialkyl ether, a polyalkylene glycol alkyl aryl ether, and a polyalkylene glycol diaryl ether.

Examples of the polyalkylene glycol dialkyl ether include diethylene glycol dialkyl ethers, such as diethylene glycol dibutyl ether, diethylene glycol dihexyl ether, diethylene glycol dioctyl ether, diethylene glycol butyl-2-chlorophenyl ether, diethylene glycol butylhexyl ether, diethylene glycol butyloctyl ether, and diethylene glycol hexyloctyl ether; triethylene glycol dialkyl ethers, such as triethylene glycol diethyl ether, triethylene glycol dipropyl ether, triethylene glycol dibutyl ether, triethylene glycol dihexyl ether, triethylene glycol dioctyl ether, triethylene glycol butyloctyl ether, triethylene glycol butyldecyl ether, triethylene glycol butylhexyl ether, and triethylene glycol hexyloctyl ether; tetraethylene glycol dialkyl ethers, such as tetraethylene glycol diethyl ether, tetraethylene glycol dipropyl ether, tetraethylene glycol dibutyl ether, tetraethylene glycol dihexyl ether, tetraethylene glycol dioctyl ether, tetraethylene glycol butylhexyl ether, tetraethylene glycol butyloctyl ether, and tetraethylene glycol hexyloctyl ether; and other polyethylene glycol dialkyl ethers. Furthermore, the polyalkylene glycol dialkyl ether also includes polypropylene glycol dialkyl ether for which an ethyleneoxy group in the polyethylene glycol dialkyl ether described above is substituted with a propyleneoxy group, and polybutylene glycol dialkyl ether for which an ethyleneoxy group in the polyethylene glycol dialkyl ether described above is substituted with a butyleneoxy group.

Examples of the polyalkylene glycol alkylaryl ether include diethylene glycol butylphenyl ether, diethylene glycol hexylphenyl ether, diethylene glycol octylphenyl ether, triethylene glycol butylphenyl ether, triethylene glycol hexylphenyl ether, triethylene glycol octylphenyl ether, tetraethylene glycol butylphenyl ether, tetraethylene glycol hexylphenyl ether, tetraethylene glycol octylphenyl ether, and polyethylene glycol alkylaryl ether for which some of hydrogen atoms of the phenyl group in these compounds are substituted with alkyl, alkoxy, or halogen atoms; polypropylene glycol alkylaryl ether for which an ethyleneoxy group in the polyalkylene glycol alkylaryl ether is substituted with a propyleneoxy group, and polybutylene glycol alkylaryl ether for which an ethyleneoxy group in the polyalkylene glycol alkylaryl ether is substituted with a butyleneoxy group.

Examples of the polyalkylene glycol diaryl ether include diethylene glycol diphenyl ether, triethylene glycol diphenyl ether, tetraethylene glycol diphenyl ether, or a polyethylene glycol diaryl ether for which some of the hydrogen atoms of the phenyl group of these compounds are substituted with alkyl, alkoxy, or halogen atoms; and a polypropylene glycol diaryl ether for which an ethyleneoxy group in the polyalkylene glycol diaryl ether is substituted with a propyleneoxy group, and a polybutylene glycol diaryl ether for which an ethyleneoxy group in the polyalkylene glycol diaryl ether is substituted with a butyleneoxy group.

Among these, from perspective of being less likely to cause thermal degradation, a polyalkylene glycol dialkyl ether is preferable, and tetraethylene glycol dibutyl ether, triethylene glycol butyloctyl ether, diethylene glycol dibutyl ether, and diethylene glycol butyl-2-chlorophenyl ether are more preferable, and from the perspective of the glycolide recovery ratio, tetraethylene glycol dibutyl ether and triethylene glycol butyloctyl ether are even more preferable.

The addition amount of the organic solvent is, for example, preferably from 30 to 5000 parts by mass, more preferably from 50 to 2000 parts by mass, and even more preferably from 100 to 1000 parts by mass, per 100 parts by mass of the glycolic acid oligomer.

When the depolymerization reaction solution contains an organic solvent, the content of the glycolic acid oligomer is preferably 1 mass % or greater and 50 mass % or less, and more preferably 15 mass % or greater and 50 mass % or less, with respect to an amount of the depolymerization reaction solution.

Other Components

In the present embodiment, the depolymerization reaction solution may optionally contain a component such as a solubilizing agent. For example, with a depolymerization reaction solution containing a solubilizing agent, the depolymerization reaction of glycolic acid oligomer can be accelerated.

Examples of such a solubilizing agent include alcohols, phenols, aliphatic carboxylic acids, aliphatic amides, and aliphatic imides. Among these, alcohols are preferred.

Examples of the alcohols include aliphatic alcohols, such as decanol, tridecanol, decanediol, ethylene glycol, propylene glycol, and glycerin; aromatic alcohols, such as cresol, chlorophenol, and naphthyl alcohol; polyalkylene glycols;

and polyalkylene glycol monoethers. One of these alcohols may be used alone, or two or more of these alcohols may be used in combination.

Preferably from 10 to 200 wt. %, more preferably from 30 to 150 wt. %, and even more preferably from 40 to 100 wt. %, of the solubilizing agent is contained with respect to an amount of the glycolic acid oligomer in the depolymerization reaction solution.

Preparation of Depolymerization Reaction Solution

The method for synthesizing the glycolic acid oligomer contained in the depolymerization reaction solution is not particularly limited, and the glycolic acid oligomer may be synthesized by a known method. Examples thereof include a method in which glycolic acid is subjected to dehydrating polycondensation, a method in which a glycolic acid ester is subjected to polycondensation, and a method of biosynthesis. Note that, in the present embodiment, the glycolic acid may be an ester (for example, a lower alkyl ester), a salt (for example, a sodium salt), or the like.

In a case where the glycolic acid is subjected to dehydrating polycondensation to synthesize the glycolic acid oligomer, preparation may be performed by supplying an aqueous solution containing glycolic acid to dehydrating polycondensation reaction. The heating temperature (dehydrating polycondensation temperature) during the dehydrating polycondensation reaction is preferably 50° C. or higher and 300° C. or lower, more preferably 100° C. or higher and 250° C. or lower, and even more preferably 140° C. or higher and 230° C. or lower.

The titanium catalyst to be contained in the depolymerization reaction solution may be added at the time of preparation of the glycolic acid oligomer or after preparation of the glycolic acid oligomer. When to add the titanium catalyst may be decided taking the method for preparing the glycolic acid oligomer into consideration. For example, in a case where a solvent containing water is used during preparation of the glycolic acid oligomer, if the titanium catalyst is added during the glycolic acid oligomer preparation, the titanium catalyst and water are reacted, and thus catalytic ability of the titanium catalyst decreases. Because of this, productivity of glycolide in the second step may deteriorate. Meanwhile, like a method in which a glycolic acid ester is subjected to polycondensation, in a case where an amount of water including formed water in the glycolic acid oligomer preparation is extremely small, the glycolic acid oligomer can be produced in a condition in which the titanium catalyst has been added.

In the present embodiment, the depolymerization reaction solution is preferably prepared by adding the titanium catalyst after the glycolic acid oligomer is prepared. According to this method, even when a process with water formation during glycolic acid oligomer synthesis is included, a suitable depolymerization reaction solution can be prepared.

From the perspective of facilitating uniform dissolution of the titanium catalyst, the addition of the titanium catalyst may be performed while agitation is performed.

Second Step

The second step is a step of producing glycolide by depolymerization of the glycolic acid oligomer in the depolymerization reaction solution prepared in the first step. The method of depolymerization of the glycolic acid oligomer may be melt depolymerization or solution depolymerization. Solution depolymerization is preferable from the perspective of being able to stably produce glycolide in large quantities. That is, depolymerization is preferably performed using a depolymerization reaction solution containing an organic solvent.

In the second step, the reaction temperature of the depolymerization reaction is only required to be not lower than the temperature at which depolymerization of the glycolic acid oligomer occurs, and while the reaction temperature depends on the degree of depressurization, the type of high boiling point organic solvent, and the like, the reaction temperature is generally 200° C. or higher, preferably 200° C. or higher and 350° C. or lower, more preferably 210° C. or higher and 310° C. or lower, even more preferably 220° C. or higher and 300° C. or lower, and yet even more preferably 230° C. or higher to 290° C. or lower.

Heating during the depolymerization reaction is preferably performed under normal pressure or under reduced pressure, and is preferably performed under a reduced pressure of 0.1 kPa or higher and 90 kPa or less. This is because the depolymerization reaction temperature decreases as the pressure is reduced, and therefore a lower pressure facilitates a reduction in the heating temperature, and the recovery ratio of the solvent is increased. The degree of depressurization is preferably 1 kPa or higher and 60 kPa or less, more preferably 1.5 kPa or higher and 40 kPa or less, and even more preferably 2 kPa or higher and 30 kPa or less.

The frequency of collection of the produced glycolide is not particularly limited, and the collection may be performed once the reaction is terminated or may be performed any time during the reaction. For example, glycolide may be collected every one hour. In a case where the depolymerization reaction solution contains a solvent, the produced glycolide may be collected by codistillation together with the solvent of the depolymerization reaction.

In a case where glycolide is collected during the reaction, the glycolic acid oligomer in an amount equivalent to the mass of the recovered glycolide is preferably added to the depolymerization reaction solution. When glycolide is collected by codistillation with the solvent, the glycolic acid oligomer and the solvent in amounts equivalent to the amounts of the collected glycolide and solvent are supplied to the depolymerization reaction solution. Note that the solvent to be recovered and the solvent to be supplied are preferably an identical solvent. Consequently, since the mass of the depolymerization reaction solution is not reduced even when glycolide is collected, the content of the titanium catalyst with respect to the amount of the depolymerization reaction solution is not increased, and thus the production speed of by-products can be made constant. With the second step including collection of glycolide and additional supply of the glycolic acid oligomer, even when the second step is continued for a long period of time, glycolide can be suitably produced without an increased production speed of by-products in the middle.

The present invention is not limited to the above-described embodiments, and various modifications can be made within the scope of the claims, and embodiments obtained by appropriately combining technical means disclosed in different embodiments are also included in the technical scope of the present invention.

SUMMARY

The present invention may be embodied as follows.

A method for producing glycolide according to the present aspect 1 includes: a first step of preparing a depolymerization reaction solution containing a glycolic acid oligomer and a titanium catalyst selected from the group consisting of organic titanium catalysts and inorganic titanium catalysts; and a second step of producing glycolide by depolymerization of the glycolic acid oligomer, a content of titanium element derived from the titanium catalyst in the depolymerization reaction solution being 1.2 mmol/L or less. By this configuration, generation of by-products can be suppressed while productivity of glycolide is improved.

The method for producing glycolide according to the present aspect 2, where, in the aspect 1 above, the content of titanium element in the depolymerization reaction solution is 0.008 mmol/L or greater.

The method for producing glycolide according to the present aspect 3, where, in the aspect 1 or 2 above, the depolymerization reaction solution contains an organic solvent.

The method for producing glycolide according to the present aspect 4, where, in the aspect 3 above, the organic solvent includes a polyalkylene glycol diether represented by Formula (1) below.

[Chemical Formula 2]

$$X—O—(—R—O—)p\text{-}Y \quad (1)$$

In Formula (1). R represents a methylene group or a linear or branched alkylene group having from 2 to 8 carbons, X and Y each independently represent an alkyl group having from 2 to 20 carbons or an aryl group, p represents an integer of 1 to 5, and when p is 2 or greater, a plurality of Rs may be the same or different.

The method for producing glycolide according to the present aspect 5, where, in any one of the aspects 1 to 4 above, the titanium catalyst is an organic titanium catalyst.

The method for producing glycolide according to the present aspect 6, where, in any one of the aspects 1 to 5 above, the depolymerization reaction solution contains a titanium alkoxide as the organic titanium catalyst.

The method for producing glycolide according to the present aspect 7, where, in any one of the aspects 1 to 6 above, in the first step, the depolymerization reaction solution is prepared by adding the titanium catalyst after the glycolic acid oligomer is prepared.

The method for producing glycolide according to the present aspect 8, where, in any one of the aspects 1 to 7 above, the second step includes: collecting produced glycolide from the depolymerization reaction solution, and adding the glycolic acid oligomer in an amount equivalent to a mass of collected glycolide into the depolymerization reaction solution.

EXAMPLES

1. Synthesis of Glycolic Acid Oligomer

Synthesis Example 1

In a 1 L separable flask, 1 kg of 70% glycolic acid aqueous solution (available from Chemours) was charged and heated while being agitated at ambient pressure, and the temperature was raised from room temperature to 220° C. over 4 hours. During this time, a condensation reaction was performed while the generated water was distilled off. Next, the pressure in the flask was gradually reduced from ambient pressure to 2 kPa over 1 hour, and then heating was performed at 220° C. for 3 hours to continue the condensation reaction. Subsequently, low-boiling point components such as unreacted raw materials were distilled off and thus 480 g of a glycolic acid oligomer was obtained.

Synthesis Example 2

480 g of the glycolic acid oligomer was obtained in the same manner as in Synthesis Example 1 except for adding iron powder during charging of the 70% glycolic acid aqueous solution. At this time, the content of iron in the glycolic acid oligomer was 30 ppm.

2. Production of Glycolide

Example 1

A container having a volume of 0.5 L was charged with 120 g of the glycolic acid oligomer prepared in Synthesis Example 1, 130 g of tetraethylene glycol dibutyl ether, and 100 g of octyltriethylene glycol, and thus 0.37 L of a reaction solution was prepared. Then, the reaction solution was heated to 235° C., and the reaction system was formed into a homogeneous solution. The pressure of the reaction system was reduced to 3 kPa, and a depolymerization reaction was performed while heating at a temperature of 235° C. Then, 1 mg of titanium tetrabutoxide (hereinafter, TB) was added, and the depolymerization reaction was further performed. At this time, the TB content was 0.01 mmol/L with respect to the total amount of the reaction solution.

During the depolymerization reaction, every one hour, tetraethylene glycol dibutyl ether and glycolide (hereinafter, referred to as "crude glycolide") were co-distilled, and the crude glycolide was separated and collected from the co-distillate. Along with the collection of crude glycolide, the glycolic acid oligomer in an amount equivalent to the mass (one-fold amount) of the collected crude glycolide was newly fed into the reaction solution. The production speed ratios of the obtained crude glycolide and methyl glycolide, which is a by-product in the crude glycolide, before and after the TB addition were measured.

Example 2

The operation was performed in the same conditions as in Example 1 except for changing the TB addition amount to 12 mg. At this time, the TB content in the reaction solution was 0.1 mmol/L with respect to the total amount of the reaction solution.

Example 3

The operation was performed in the same conditions as in Example 1 except for changing the TB addition amount to 20 mg. At this time, the TB content in the reaction solution was 0.2 mmol/L with respect to the total amount of the reaction solution.

Example 4

The operation was performed in the same conditions as in Example 1 except for changing the TB addition amount to 35 mg. At this time, the TB content in the reaction solution was 0.3 mmol/L with respect to the total amount of the reaction solution.

Example 5

The operation was performed in the same conditions as in Example 1 except for changing the TB addition amount to 50 mg. At this time, the TB content in the reaction solution was 0.4 mmol/L with respect to the total amount of the reaction solution.

Example 6

The operation was performed in the same conditions as in Example 1 except for changing the TB addition amount to 121 mg. At this time, the TB content in the reaction solution was 1.0 mmol/L with respect to the total amount of the reaction solution.

Comparative Example 1

The operation was performed in the same conditions as in Example 1 except for adding no TB.

Comparative Example 2

The operation was performed in the same conditions as in Example 1 except for using the glycolic acid oligomer obtained in Synthesis Example 2 in place of the glycolic acid oligomer obtained in Synthesis Example 1, and adding no TB.

Comparative Example 3

The operation was performed in the same conditions as in Example 1 except for changing the TB addition amount to 152 mg. At this time, the TB content in the reaction solution was 1.3 mmol/L with respect to the total amount of the reaction solution.

Comparative Example 4

The operation was performed in the same conditions as in Example 1 except for changing the TB addition amount to 263 mg. At this time, the TB content in the reaction solution was 2.1 mmol/L with respect to the total amount of the reaction solution.

3. Evaluation of Production Speed Ratio of Crude Glycolide and By-Product

For Examples 1 to 5 and Comparative Examples 1 to 4, arithmetic means of the amount of the crude glycolide collected per 1 hour and the content of the by-product contained in the crude glycolide were determined and designated as the production speed (g/h) of the crude glycolide and the content (wt. %/h) of the by-product in the crude glycolide. The crude glycolide production speed ratios and the by-product production speed ratios of Examples 1 to 5 and Comparative Examples 2 to 4 were each calculated by dividing a production speed of each product after the catalyst addition by a production speed of each product before the catalyst addition. For Comparative Example 1 in which no catalyst was added, since there were no changes in the crude glycolide production speed ratio and the by-product production speed ratio due to the catalyst addition, the crude glycolide production speed ratio and the by-product production speed ratio were each considered as 1.0.

The crude glycolide production speed ratios and the by-product production speed ratios of Examples 1 to 6 and Comparative Examples 1 to 4 are shown in Table 1.

TABLE 1

| | | | Crude glycolide | | Byproduct | |
|---|---|---|---|---|---|---|
| | Catalyst | Catalyst content (mmol/L) | Production speed (g/h) | Production speed ratio due to catalyst addition | Content in crude glycolide (wt. %/h) | Production speed ratio due to catalyst addition |
| Example 1 | TB | 0.01 | 7.2 | 1.1 | 0.57 | 0.95 |
| Example 2 | TB | 0.1 | 8.0 | 1.2 | 0.59 | 0.98 |
| Example 3 | TB | 0.2 | 8.5 | 1.3 | 0.60 | 1.00 |
| Example 4 | TB | 0.3 | 8.6 | 1.3 | 0.61 | 1.02 |
| Example 5 | TB | 0.4 | 9.0 | 1.3 | 0.62 | 1.03 |
| Example 6 | TB | 1.0 | 8.8 | 1.3 | 0.61 | 1.02 |
| Comparative Example 1 | — | — | 6.7 | 1.0 | 0.60 | 1.00 |
| Comparative Example 2 | Fe | 0.2 | 7.4 | 1.1 | 0.90 | 1.50 |
| Comparative Example 3 | TB | 1.3 | 8.9 | 1.3 | 1.00 | 1.67 |
| Comparative Example 4 | TB | 2.2 | 8.8 | 1.3 | 1.90 | 3.17 |

As listed in Table 1, in the case where the TB content in the reaction solution was 1.3 mmol/L or greater, the production speed of the by-product increased along with an increase of the addition amount. On the other hand, in the case where the TB content in the reaction solution was less than 1.3 mmol/L, the production speed of the by-product decreased to a level equivalent to that in the case where no catalyst was added, and the productivity of the crude glycolide increased.

INDUSTRIAL APPLICABILITY

The present invention can be used in production of glycolide.

The invention claimed is:

1. A method for producing glycolide, the method comprising:

a first step of preparing a depolymerization reaction solution containing a glycolic acid oligomer, and a titanium alkoxide catalyst; and a second step of producing glycolide by depolymerization of the glycolic acid oligomer, a content of titanium element derived from the titanium alkoxide catalyst in the depolymerization reaction solution being 1.2 mmol/L or less.

2. The method for producing glycolide according to claim 1, wherein the content of titanium element in the depolymerization reaction solution is 0.008 mmol/L or greater.

3. The method for producing glycolide according to claim 1, wherein the depolymerization reaction solution contains an organic solvent.

4. The method for producing glycolide according to claim 3, wherein the organic solvent includes a polyalkylene glycol diether represented by Formula (1) below:

$$X—O—(—R—O—)p\text{-}Y \quad (1)$$

wherein R represents a methylene group or a linear or branched alkylene group having from 2 to 8 carbons, X and Y each independently represent an alkyl group having from 2 to 20 carbons or an aryl group, p represents an integer of 1 to 5, and when p is 2 or greater, a plurality of Rs are the same or different.

5. The method for producing glycolide according to claim 1, wherein, in the first step, the depolymerization reaction solution is prepared by adding the titanium alkoxide catalyst after the glycolic acid oligomer is prepared.

6. The method for producing glycolide according to claim 1, wherein the second step comprises:

collecting produced glycolide from the depolymerization reaction solution, and adding the glycolic acid oligomer in an amount equivalent to a mass of collected glycolide into the depolymerization reaction solution.

* * * * *